United States Patent [19]

Ishijima

[11] Patent Number: 5,409,714
[45] Date of Patent: Apr. 25, 1995

[54] ANTIMICROBIAL AGENT AND METHOD FOR SUSTAINING FRESHNESS OF FOOD

[75] Inventor: Ichiro Ishijima, Tokyo, Japan

[73] Assignee: Kaiho Co., Ltd., Japan

[21] Appl. No.: 104,037

[22] PCT Filed: Dec. 14, 1992

[86] PCT No.: PCT/JP92/01624
§ 371 Date: Aug. 9, 1993
§ 102(e) Date: Aug. 9, 1993

[87] PCT Pub. No.: WO93/11670
PCT Pub. Date: Jun. 24, 1993

[30] Foreign Application Priority Data

Dec. 16, 1991 [JP] Japan .................. 3-352698

[51] Int. Cl.$^6$ .................. A61K 33/08; A61K 33/06
[52] U.S. Cl. .................. 424/693; 423/173; 423/175; 424/688; 426/532
[58] Field of Search .................. 424/693, 688; 423/175, 423/173; 426/532

[56] References Cited

U.S. PATENT DOCUMENTS

| | | | |
|---|---|---|---|
| 4,684,529 | 8/1987 | Ueno | 426/237 |
| 4,988,520 | 1/1991 | Overton | 426/74 |
| 5,215,769 | 6/1993 | Fox et al. | 426/74 |
| 5,296,246 | 3/1994 | Inoue et al. | 426/74 |
| 5,344,636 | 9/1994 | Miyata | 424/693 |

FOREIGN PATENT DOCUMENTS

| | | |
|---|---|---|
| 63280 | 1/1988 | Japan . |
| 1117833 | 5/1989 | Japan . |
| 377802 | 4/1991 | Japan . |
| 3148225 | 6/1991 | Japan . |

OTHER PUBLICATIONS

Chem. Abstracts, Derwent Abstracts of Japanese Patents cited by Applicant.
Shinohara GA.116;127400z (1991) of JP 03291230 (Dec. 20, 1991).
Ueda CA116:82525a (1991) of JP 03240449 (Oct. 25, 1991).
Moriyama GA91:173708u 1979 of JP 5408665y (Jul. 10, 1979).
Kurokawa CA 80:58636e (1973) of JP 48085721 (Nov. 13, 1973) (Derwent Abstr).
Kaiko Derwent Abstract of JP 78-73367 (Jun. 17, 1978).
Kaji Derwent Abstr. of JP 52110878 (Sep. 17, 1979).
Fujiex Derwent Abstr. of JP5262655 (Mar. 7, 1992).

Primary Examiner—Shep K. Rose
Attorney, Agent, or Firm—Lorusso & Loud

[57] ABSTRACT

An antimicrobial agent contains a calcined product of a calcium oxide type prepared by calcining shells of an oyster and/or a calcined product of a calcium hydroxide type as a hydrate of the calcined product of the calcium oxide type.

14 Claims, No Drawings

ANTIMICROBIAL AGENT AND METHOD FOR SUSTAINING FRESHNESS OF FOOD

TECHNICAL FIELD

The present invention relates to an antimicrobial agent and a method for sustaining the degree of freshness of food.

BACKGROUND ART

Fungi may appear in various kinds of food and industrial products such as paints, paste, and so on. Once the fungi appear in the food and the industrial products, the commercial value of the goods is damaged to a great extent and they are caused to be thrown away in many cases. Even if the fungi would not appear, the growth or the propagation of hazardous microorganisms may damage the commercial value of the goods to a remarkable extent and cause the goods to be thrown away in some cases. Further, the growth or the propagation of such microorganisms in food may cause food poison.

Heretofore, as an antimicrobial agent superior in safety for the human body and applicable to food, ethanol, a hypochlorite, and an allylisothiocyanate are mainly employed. However, ethanol is an inflammable liquid so that the requirement for caution in handling is a weak point. The hypochlorite has the defect that it generates an unpleasant odor derived from chlorine. The allylisothiocyanate presents the defects that it is decomposed in water, generating a malodorous smell, and it is strongly irritating as well.

The main object of the present invention is to provide an antimicrobial agent which is highly safe for the human body, which is easy to handle, and which does not generate any unpleasant odor.

Another object of the present invention is to provide a method for sustaining the degree of freshness of food.

Other objects, features and advantages of the present invention will become apparent during the course of the disclosure of the invention which follows.

DISCLOSURE OF INVENTION

As a result of extensive studies and research on the development of antimicrobial agents which are highly safe for the human body, which are easy to handle, and which do not cause any unpleasant odor upon application, it has surprisingly been found by the present inventor that a calcined product obtained by calcining shells of an oyster has a highly antimicrobial action and, further, that food treated with the calcined product can sustain the high degree of freshness.

The present invention provides the antimicrobial agent comprising a calcined product of a calcium oxide type, prepared by calcining the shells of the oyster, and/or a calcined product of a calcium hydroxide type which is in the form of a hydrate of the calcined product of the calcium oxide type.

The present invention further provides the method for sustaining the degree of freshness of food by having the calcined product contained in the food.

In addition, the present invention provides the method for sustaining the degree of freshness of food by bringing the food into contact with an aqueous solution or an aqueous dispersion, each containing the calcined product.

It is to be noted herein that the term "antimicrobial action" and its related terms are intended to encompass a germicidal action and a germistatic action. Further, the term "germ" and its related terms are intended to encompass bacteria, fungi, spores thereof, algae and other hazardous microorganisms.

The antimicrobial agent according to the present invention comprises a calcined product of the shells of an oyster or Ostracea. More specifically, the oyster may include, for example, Ostrea, Crassostrea, Sexostrea, and so on. The calcined product may be prepared by calcining the shells of the oyster at high temperatures of approximately 600° C. or higher, preferably in the range of from 900° C. to 1,200° C. As the atmosphere in which the shells of the oyster are calcined, air is usually employed; however, an inert gas such as nitrogen or argon may be employed. The time of calcination may range usually from 15 minutes to 60 minutes, preferably from 20 minutes to 45 minutes. The calcination may be carried out preferably by generating heat (Joule's heat) upon application of electric current to the shells of the oyster employed as a resistor, thereby calcining the shells of the oyster with the heat generated.

The calcination of the shells of the oyster in the manner as described hereinabove causes organic materials of the shells of the oyster to be thermally decomposed and then removed, thereby giving a product of a white or grayish white color. The calcined product is then divided into fine powders having a desired range of grain sizes. The calcined product contains calcium oxide as a major ingredient in the range of from 60% to 80% by weight, preferably from 65% to 75% by weight, when translated into Ca, and, as minute ingredients, magnesium in the range of from 3,000 to 6,000 wtppm, preferably from 3,500 to 5,500 wtppm; iron in the range of from 350 to 650 wtppm, preferably from 400 to 600 wtppm; phosphorus in the range of from 100 to 300 wtppm, preferably from 150 to 250 wtppm; potassium in the range of from 40 to 150 wtppm, preferably from 50 to 100 wtppm; sodium in the range of from 0.5 to 10 wtppm, preferably from 1 to 5 wtppm; and heavy metals in the range of from 0.5 to 5 wtppm, preferably from 1 to 3 wtppm. The pH of a saturated aqueous solution of the calcined product may be in the range of from approximately 12 to 13.

The calcined product according to the present invention may include, for example, powders having average particle sizes of 74 μm (200 mesh) or smaller, preferably 43 μm (325 mesh) or smaller.

The calcined product may be treated as a product in the form of a hydrate by having water absorbed in at least a portion thereof. The resulting hydrate contains calcium hydroxide as a major ingredient.

In accordance with the present invention, it is preferred to use the calcined product in a mixture of the calcined product of the calcium oxide type with the calcined product of the calcium hydroxide hydrate type. As the calcined product of the calcium oxide type alone is so high in alkalinity and highly hygroscopic that it is poor to handle; however, the problems can be solved by admixing the calcined product of the calcium oxide type with the calcined product of the calcium hydroxide type. The ratio of the weight of the calcined product of the calcium oxide type to the weight of the calcined product of the calcium hydroxide type may range from approximately 3 to 7 to approximately 7 to 3, preferably from approximately 4 to 6 to approximately 6 to 4.

It is advantageous to use the calcined product prepared by calcination at lower temperatures in the range of from approximately 600° to 900° C., preferably from approximately 750° to 850° C. in combination with the calcined product prepared by calcination at higher temperatures in the range of from approximately 900° to 1,200° C., preferably from 1,000° to 1,150° C. It can be noted herein that the calcined products calcined at the lower temperatures and the calcined products calcined at the higher temperatures are different in properties to a considerable extent from each other. For instance, the calcined products calcined at the lower temperatures are lower in alkalinity than the calcined products calcined at the higher temperatures and superior in handling to the latter. Hence, the mixture of the former with the latter can provide products superior in handling. The ratio of the weight of the calcined product calcined at the lower temperatures to the calcined product calcined at the higher temperatures may be in the range of from approximately 3 to 7 to approximately 7 to 3, preferably from approximately 4 to 6 to approximately 6 to 4.

The calcium oxide-type calcined product and/or the calcium hydroxide-type calcined product according to the present invention will sometimes be referred to hereinafter merely as the calcined product and it is to be understood that the calcined product is intended to mean the calcium oxide-type calcined product and/or the calcium hydroxide-type calcined product according to the present invention unless otherwise stated or if the term does not cause any misunderstanding. The calcined product according to the present invention may additionally contain, as a filler, an additive harmless to food and the human body. The additive may include, for example, powders of inorganic compounds, such as silica, alumina, magnesia, calcium oxide, a hydrate thereof, magnesium carbonate, calcium carbonate, and so on. Further, it is possible to add finely divided oyster shells of the calcium carbonate type prepared by pulverizing the dry shells of the oyster. The amount of the additive may range from approximately 10 parts to 400 parts by weight, preferably from approximately 50 parts to 200 parts by weight with respect to 100 parts by weight of the calcined product according to the present invention.

As described hereinabove, the calcined product according to the present invention demonstrates an excellent antimicrobial action. The fact that the calcined product according to the present invention has the excellently high antimicrobial action was discovered for the first time by the present inventors. Until now, the reasons for the high antimicrobial action of the calcined product according to the present invention are not yet clarified, although it is considered that some minute metallic ingredients contained in the shells of the oyster may exert some influence in imparting the antimicrobial action.

The calcined product according to the present invention may be employed in the form of powders, an aqueous solution or an aqueous dispersion.

Further, the calcined product according to the present invention may be employed advantageously as antimicrobial agents for food, for industrial uses, and for medicinal uses.

In addition, the calcined product of the calcium oxide type and/or the calcined product of the calcium hydroxide type according to the present invention may be used advantageously as an agent for sustaining the degree of freshness of food. In order to use the calcined product according to the present invention as the agent for sustaining the degree of freshness of the food, the calcined product may be admixed with and dispersed in the food or brought into contact with the food in the form of an aqueous solution or an aqueous dispersion. The aqueous solution and the aqueous dispersion may contain, as needed or as requested, an appropriate quantity of an alcohol, such as ethanol, isopropyl alcohol, glycerin, polyethylene glycol, propylene glycol, sugar alcohol, and so on. When the calcined product according to the present invention is employed in the form of the aqueous solution or the aqueous dispersion, each being prepared by adding water to the calcined product, the concentration of the calcined product in the aqueous solution or the aqueous dispersion is usually approximately 0.01% by weight or more, preferably 0.1% by weight or more. The upper limit of the concentration of the calcined product is not restricted; however, generally, the concentration thereof may be up to approximately 30% by weight or lower. It is preferred to use the calcined product in the aqueous solution or the aqueous dispersion in the amount ranging usually from 0.05% to 10% by weight, preferably from 0.1% to 5% by weight.

The calcined product according to the present invention may be applied to various kinds of food. The term "food" referred to herein is intended to mean any food, including processed food in a liquid or solid state, raw meat of livestock, fish, raw fish meat, raw shellfish, vegetables, edible roots, fruits, and so on.

When the calcined product according to the present invention is applied to the processed food in the liquid state and in the solid state, the calcined product may be admixed with and dispersed in the food in the amount ranging usually from approximately 0.05% to 10% by weight, preferably from 0.1% to 5% by weight. The calcined product in the aqueous solution or aqueous dispersion may be sprayed on the surface of the food, thereby sterilizing the hazardous microorganisms and sustaining the food at a high degree of freshness.

Further, when the calcined product according to the present invention is applied to fresh food such as the meat of the livestock, fish, raw fish meat, raw shellfish, vegetables, edible roots, fruits, and so on, the calcined product may be brought into contact with the fresh food, in the form of the aqueous solution or the aqueous dispersion which may contain the calcined product in the amount in the range of from approximately 0.05% to 10% by weight, preferably from 0.1% to 5% by weight. As the procedures for contacting the food with the calcined product, there may be included, for example, a method for immersing the fresh food in the aqueous solution of the calcined product or the aqueous dispersion thereof or a method for spraying the food with the aqueous solution thereof or the aqueous dispersion thereof.

In addition, when the calcined product according to the present invention is applied to the food immersed in an aqueous solution, for example, raw shellfish immersed in salty water or fish egg immersed in seasonings, the calcined product may be added to the aqueous solution in the amount ranging usually from 50 wtppm to 1% by weight, preferably 100 ppm to 0.5% by weight.

The calcined product according to the present invention may be employed as the antimicrobial agents for food, industrial purposes and medical use on the basis of the superior antimicrobial action of the calcined product. Further, the calcined product may advantageously be used as the agent for sustaining the degree of freshness of food. By applying the calcined product to the food as the agent for sustaining the degree of freshness of the food, the calcined product can suppress the growth or the propagation of the hazardous microorganisms adhering to the surface of the food or sterilizing them, thereby preventing the food from decaying and sustaining the food at a high degree of freshness.

EXAMPLE 1

The shells of natural Japanese oyster (*Crassosterea gigas.*) were calcined with Joule's heat at approximately 1,100° C., and the resulting calcined product was pulverized into fine particles (350 mesh; 9.0% by weight or more). The fine particles were found to contain calcium oxide as a major ingredient. The result of the elemental analysis is as follows:

Ca: 68% by weight; Mg: 489 mg/100 grams;
Fe: 47 mg/100 grams; P: 10 mg/100 grams;
Heavy metals: 2.1 wtppm; K: 7 mg/100 grams;
Na: 2 mg/100 grams The pH of a saturated aqueous solution of the calcined product used in this example was 12.4.

EXAMPLE 2

The calcined product A, prepared in Example 1, and agar culture media were autoclaved separately while applying heat. The composition of the agar culture medium was as follows:

(Agar culture medium)
Beef meat extract: 3 parts by weight
Peptone: 5 parts by weight
Agar: 15 parts by weight Then, the agar culture medium was mixed with and dispersed homogeneously in the calcined product A at a temperature as high as 40° to 50° C. in the concentration of 0.5% by weight. The dispersion was poured into Petri dishes in the amount of approximately 20 ml per each Petri dish and allowed to solidify.

The surface of the agar culture medium in the Petri dish was then coated uniformly with physiological saline containing an inoculant of germs as will be described hereinafter. The inoculating germs were as follows:

(Inoculating germs)
Germ I: *Salmonella enteritidis*
Germ II: *Escherichia coli*

Then, the Petri dish was allowed to stand at 37° C. for given periods of time and the number of germs grown on the agar culture medium was counted. The results are shown in Table 1 below.

TABLE 1

| ADDITIVE | NO. OF GERMS (GERMS PER GRAM) | | |
|---|---|---|---|
| | INITIAL | DAY 3 | DAY 7 |
| | GERM I | | |
| CALCINED PRODUCT A | $2.5 \times 10^4$ | 0.1 | 12 |
| NONE | $2.5 \times 10^4$ | $>10^5$ | — |
| | GERM II | | |
| CALCINED PRODUCT A | $4.0 \times 10^4$ | 0.1 | 14 |
| NONE | $4.0 \times 10^4$ | $>10^8$ | — |

EXAMPLE 3

Tests were carried out with inoculants of germs as will be described in Table 2 below in substantially the same manner as in Example 2 by varying the amount of the calcined product A as well as the incubation temperatures and periods of time. In Test (i), the culture medium was incubated at 10° C. for 2 weeks; and, in Test (ii), the culture medium was incubated at 37° C. for 48 hours. After the completion of the tests, the number of living germs grown on the culture medium was counted.

Further, the minimum inhibitory concentrations (MICs) of the calcined product A against the germs as will be described in Table 2 below were computed on the basis of the number of the living germs counted. The results are also shown in Table 2 below.

TABLE 2

| INOCULATING GERMS | MIC (% BY WEIGHT) | |
|---|---|---|
| | TEST (i) | TEST (ii) |
| *Salmonella typhimurium* | 0.25 | 0.1 |
| *Salmonella enteritides* | 0.25 | 0.1 |
| *Escherichia coli* | 0.25 | 0.1 |
| *Staphylococcus aureus* | 0.15 | 0.1 |
| *Bacillus subtilis* | 0.15 | 0.1 |

EXAMPLE 4

The powders of the calcined product A (0.5 gram or 0.5 gram), prepared in Example 1, were added to shucked oyster immersed in water (wet weight of the shucked oyster: 700 grams; water: 300 grams), thereby giving a dispersion which in turn was packed in a vinyl chloride package bag. As a comparison, the shucked oyster immersed in water containing no calcined product was packed in a vinyl chloride package bag in the same manner as described hereinabove.

The package bags were held at the temperature of 10° C. or lower for given periods of time. The standard plate counts were measured at day 0, week 1, and week 2 in accordance with standard procedures for testing food. The results are shown in Table 3 below.

TABLE 3

| AMOUNT OF CALCINED PRODUCT A | STANDARD PLATE COUNT (COUNTS PER GRAM) | | |
|---|---|---|---|
| (grams per kg) | DAY 0 | WEEK 1 | WEEK 2 |
| NOT ADDED | $1.9 \times 10^4$ | $4.9 \times 10^4$ | $1.5 \times 10^9$ |
| 0.2 | $3.1 \times 10^3$ | $2.2 \times 10^3$ | $9.0 \times 10^3$ |
| 0.5 | $1.3 \times 10^3$ | $2.0 \times 10^3$ | $6.0 \times 10^3$ |

EXAMPLE 5

The procedures were followed in substantially the same manner as in Example 4, except for the use of 1,000 grams of noodle containing sea weeds in place of the dispersion of the shucked oyster in water. The results are shown in Table 5 below.

TABLE 5

| AMOUNT OF CALCINED PRODUCT A | STANDARD PLATE COUNT (COUNTS PER GRAM) | | |
|---|---|---|---|
| (grams per kg) | DAY 0 | WEEK 1 | WEEK 2 |
| NOT ADDED | $1.3 \times 10^6$ | $1.9 \times 10^7$ | $1.1 \times 10^8$ |
| 0.2 | $2.2 \times 10^3$ | $6.0 \times 10^3$ | $1.5 \times 10^4$ |
| 0.5 | $1.6 \times 10^3$ | $4.2 \times 10^3$ | $6.7 \times 10^3$ |

EXAMPLE 6

Japanese-style noodles, buckwheat vermicelli noodles, and Chinese-style noodles were prepared by using 10 kg of wheat flour with 30 grams of the calcined product A added thereto. These products were then tested for measuring the degree of freshness. As a control, the products were used which were prepared in the same manner as described hereinabove, except for the addition of no calcined product. For the tests, the test samples were packed in vinyl chloride package bags and allowed to stand at 10° C. or lower for given periods of time as will be described hereinafter. The results are shown in Table 6 below. In the Table 6, noodle A stands for Japanese-style noodles not boiled; noodle B for Japanese-style noodles boiled; soba A for buckwheat vermicelli noodles not boiled; soba B for buckwheat vermicelli noodles boiled; and Chinese noodles for Chinese-style noodles not boiled.

TABLE 6

| SAMPLE | AMOUNT OF CALCINED PRODUCT A (grams per 10 kg) | STANDARD PLATE COUNT (COUNTS PER GRAM) | | |
|---|---|---|---|---|
| | | DAY 1 | DAY 3 | DAY 6 |
| NOODLE A | NONE | $6.7 \times 10^5$ | $5.4 \times 10^6$ | $1.5 \times 10^8$ |
| NOODLE B | NONE | $1.2 \times 10^5$ | $8.6 \times 10^6$ | $4.9 \times 10^8$ |
| NOODLE A | 30 | $1.5 \times 10^4$ | $2.8 \times 10^4$ | $4.3 \times 10^4$ |
| NOODLE B | 30 | $1.6 \times 10^3$ | $7.6 \times 10^5$ | $1.8 \times 10^7$ |
| SOBA A | NONE | $3.4 \times 10^6$ | $9.3 \times 10^6$ | $1.3 \times 10^8$ |
| SOBA B | NONE | $1.3 \times 10^5$ | $1.9 \times 10^5$ | $9.0 \times 10^8$ |
| SOBA A | 30 | $2.3 \times 10^4$ | $4.3 \times 10^5$ | $3.5 \times 10^6$ |
| SOBA B | 30 | $4.2 \times 10^3$ | — | $1.1 \times 10^5$ |
| CHINESE NOODLES | NONE | $5.4 \times 10^4$ | $6.8 \times 10^4$ | $3.6 \times 10^5$ |
| CHINESE NOODLES | 30 | $6.0 \times 10^2$ | $4.2 \times 10^3$ | $5.7 \times 10^4$ |

EXAMPLE 7

To vanilla ice creams was added the calcined product A in the amount of 0.1% by weight, and the ice creams were allowed to stand at 0° C. or below for 10 days. After the storage for 10 days, the standard plate count indicated 300 germs per gram or lower.

For comparative purposes, vanilla ice creams with no calcined product added thereto were stored under the same conditions as described hereinabove. The standard plate count indicated 830 germs per gram.

EXAMPLE 8

A cucumber was washed with water without cutting and immersed for 2 hours at room temperature in an aqueous solution containing the calcined product A in the amount of 0.5% by weight. The cucumber was then tested for the standard plate count. The number of the germs was $2.7 \times 10^3$ germs per gram.

For comparative purposes, a cucumber was washed with water without cutting and immersed for 2 hours at room temperature in an aqueous solution containing no calcined product. The cucumber was then tested for the standard plate count. The number of the germs was $1.6 \times 10^6$ germs per gram.

EXAMPLE 9

A cut cabbage was washed with water and immersed for 2 hours at room temperature in an aqueous solution containing the calcined product A in the amount of 0.5% by weight. The cucumber was then tested for the standard plate count. The number of the germs was $9.8 \times 10^3$ germs per gram.

For comparative purposes, a cut cabbage was washed with water without cutting and immersed for 2 hours at room temperature in an aqueous solution containing no calcined product. The cucumber was then tested for the standard plate count. The number of the germs was $1.1 \times 10^6$ germs per gram.

EXAMPLE 10

To a raw egg was added the calcined product A in the amount of 0.2% by weight, and the egg was scrambled. The scrambled eggs were then allowed to stand at 5° C. for 7 days and tested for the standard plate count. As a result, it was found that they contained 100 counts of germs per gram or lower. It is thus confirmed that the addition of the calcined product A allows the scrambled eggs to be stored with maintenance of a high degree of freshness.

EXAMPLE 11

A cuttlefish was stored at 5° C. for 7 days in an aqueous solution containing the calcined product A in the amount of 0.2% by weight and then tested for the standard plate count. As a result, it was found that it contained 30 counts of germs per gram or lower.

On the other hand, for comparative purposes, a cuttlefish was stored at 5° C. for 7 days in water containing no calcined product A. As a result, it was found that it contained $1.2 \times 10^8$ counts of germs per gram or lower.

EXAMPLE 12

An edible jellyfish with 100 counts of germs per gram or lower was immersed in an aqueous solution containing the calcined product A in the amount of 0.2% by weight and stored at 5° C. for 7 days. As a result, it was found that it contained 100 counts of germs per gram or lower, when measured for the standard plate count. It is thus confirmed that the stored fresh jellyfish maintained a high degree of freshness.

What is claimed is:

1. An antimicrobial agent comprising (a) a calcined product, containing a major portion of calcium oxide and prepared by calcining oyster shells and (b) a hydrated product containing a major portion of calcium hydroxide and prepared by calcining oyster shells and then hydrating.

2. An antimicrobial agent according to claim 1, wherein the ratio of (a) to (b) is 3/7 to 7/3.

3. An antimicrobial agent according to claim 1, wherein both the calcined product (a) and hydrated product (b) have an average particle size of 74 μm or less.

4. An antimicrobial agent according to claim 1, wherein a first portion of said products is prepared with calcining at 750°–850° C. and a second portion of said products is prepared with calcining at 1000°–1150° C.

5. A process for the preparation of an antimicrobial agent according to claim 1, which comprises calcining oyster shells to produce a calcined product and hydrating a part of the calcined product by contacting the calcined product with water.

6. A process for the preparation of an antimicrobial agent according to claim 5 wherein a first portion of said calcined product is prepared by calcining at 750°–850° C. and a second portion of said calcined product is prepared by calcining at 1000°–1150° C.

7. A process for the preparation of an antimicrobial agent according to claim 2, which comprises calcining oyster shells to produce a calcined product and hydrating a part of the calcined product by contacting the calcined product with water.

8. A method for sustaining freshness of food comprising adding an antimicrobial agent as claimed in claim 1 to the food.

9. The method for sustaining freshness of food of claim 8 wherein said antimicrobial agent is added to the food by contacting the food with an aqueous solution or dispersion of the antimicrobial agent.

10. The method for sustaining freshness of food of claim 8, wherein said adding is by admixing the antimicrobial agent with the foodstuff.

11. A method for suppressing the growth of bacteria in a foodstuff comprising adding to the foodstuff an antimicrobial agent comprising (a) a calcined product, containing a major portion of calcium oxide and prepared by calcining oyster shells and (b) a hydrated product containing a major portion of calcium hydroxide and prepared by calcining oyster shells and then hydrating.

12. The method of claim 11 wherein said adding is by contacting the food with an aqueous solution or dispersion of the antimicrobial agent.

13. The method of claim 11 wherein said adding is by admixing the antimicrobial agent with the food.

14. The method of claim 11 wherein said bacteria, the growth of which is suppressed, include at least one member selected from the group consisting of *Salmonella typhimurium, Salmonella enteritides, Escherichia coli, Staphylococcus aureus* and *Bacillus subtilis*.

* * * * *

UNITED STATES PATENT AND TRADEMARK OFFICE
CERTIFICATE OF CORRECTION

PATENT NO. : 5,409,714
DATED : April 25, 1995
INVENTOR(S) : Ichiro ISHIJIMA

It is certified that error appears in the above-indentified patent and that said Letters Patent is hereby corrected as shown below:

Col. 5, line 14, "9.0%" should read --90%--.

Signed and Sealed this

Eighteenth Day of February, 1997

Attest:

BRUCE LEHMAN

*Attesting Officer*  *Commissioner of Patents and Trademarks*